(12) United States Patent
Selkee

(10) Patent No.: US 8,374,670 B2
(45) Date of Patent: Feb. 12, 2013

(54) CATHETER HAVING A FORCE SENSING DISTAL TIP

(75) Inventor: Thomas V. Selkee, Claremont, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 39 days.

(21) Appl. No.: 12/692,506

(22) Filed: Jan. 22, 2010

(65) Prior Publication Data

US 2011/0184406 A1    Jul. 28, 2011

(51) Int. Cl.
   *A61B 5/042*    (2006.01)
   *A61B 18/14*    (2006.01)
(52) U.S. Cl. .......................... 600/374; 606/41
(58) Field of Classification Search ............ 600/374; 606/41
   See application file for complete search history.

(56) References Cited

U.S. PATENT DOCUMENTS

| | | |
|---|---|---|
| 3,971,364 A | 7/1976 | Fletcher et al. |
| 4,764,114 A | 8/1988 | Jeffcoat et al. |
| 4,856,993 A | 8/1989 | Maness et al. |
| 5,263,493 A | 11/1993 | Avitall |
| 5,368,564 A | 11/1994 | Savage |
| 5,391,199 A | 2/1995 | Ben-Haim |
| 5,487,757 A * | 1/1996 | Truckai et al. ............ 604/264 |
| 5,499,542 A | 3/1996 | Morlan |
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,769,843 A | 6/1998 | Abela et al. |
| 5,826,576 A | 10/1998 | West |

(Continued)

FOREIGN PATENT DOCUMENTS

| | | |
|---|---|---|
| DE | 19750441 A1 | 6/1999 |
| EP | 0 928 601 A1 | 7/1999 |

(Continued)

OTHER PUBLICATIONS

European Patent Office, Extended European Search Report, Application No. 11250066.5, dated Sep. 20, 2011, 12 pgs.

(Continued)

*Primary Examiner* — Lee Cohen
(74) *Attorney, Agent, or Firm* — Christie, Parker & Hale, LLP

(57) ABSTRACT

A mapping and ablation catheter with contact force sensing capabilities at a distal end, includes a catheter body, a deflectable section, and a tip distal section which has a tip electrode and a contact force sensor for sensing a 3D contact force vector applied to the tip electrode. In contact with the tip electrode, the contact force sensor has a body and has at least one sensor with an electrical characteristic that is responsive to deformation of the body resulting from force vector. The sensor is adapted to receive an electrical current and to output an electrical signal indicative of a change in the electrical characteristic. In one embodiment, the sensor is a strain gage responsive to tension and compression of at least a portion of the body of the force sensor and the electrical characteristic of the strain gage that is monitored is electrical resistivity. In another embodiment, the sensor is responsive to strain and stress of at least a portion of the body, and the electrical characteristic being monitored is inductance or hysteresis loss.

7 Claims, 14 Drawing Sheets

U.S. PATENT DOCUMENTS

| | | |
|---|---|---|
| 5,833,608 A | 11/1998 | Acker |
| 5,836,894 A | 11/1998 | Sarvazyan |
| 5,860,974 A | 1/1999 | Abele |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,983,126 A | 11/1999 | Wittkampf |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,335,617 B1 | 1/2002 | Osadchy et al. |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Muller et al. |
| 6,814,733 B2 | 11/2004 | Schwartz et al. |
| 6,835,173 B2 | 12/2004 | Couvillon, Jr. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,306,593 B2 | 12/2007 | Keidar et al. |
| 7,311,704 B2 | 12/2007 | Paul et al. |
| 7,397,364 B2 | 7/2008 | Govari |
| 7,481,774 B2 | 1/2009 | Brockway et al. |
| 7,536,218 B2 | 5/2009 | Govari et al. |
| 7,604,605 B2 | 10/2009 | Zvuloni |
| 7,681,432 B2 | 3/2010 | Hay et al. |
| 7,686,767 B2 | 3/2010 | Maschke |
| 8,083,691 B2 | 12/2011 | Goldenberg et al. |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0173480 A1 | 8/2006 | Zhang |
| 2006/0200049 A1 | 9/2006 | Leo et al. |
| 2006/0247618 A1 | 11/2006 | Kaplan et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0183075 A1 | 7/2008 | Govari et al. |
| 2008/0249522 A1 | 10/2008 | Pappone et al. |
| 2008/0255540 A1 | 10/2008 | Selkee |
| 2008/0275428 A1 | 11/2008 | Tegg et al. |
| 2008/0275442 A1* | 11/2008 | Paul et al. .................... 606/41 |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0287118 A1 | 11/2009 | Malek |
| 2009/0306650 A1 | 12/2009 | Govari et al. |
| 2010/0063478 A1 | 3/2010 | Selkee |
| 2010/0137845 A1 | 6/2010 | Ramstein et al. |
| 2010/0152574 A1 | 6/2010 | Erdman et al. |
| 2010/0168620 A1 | 7/2010 | Klimovitch et al. |
| 2010/0168918 A1 | 7/2010 | Zhao et al. |
| 2011/0130648 A1 | 6/2011 | Beeckler et al. |
| 2011/0184406 A1 | 7/2011 | Selkee |

FOREIGN PATENT DOCUMENTS

| | | |
|---|---|---|
| EP | 2 338 411 A1 | 6/2001 |
| EP | 1 502 555 A1 | 2/2005 |
| EP | 1 586 281 A1 | 10/2005 |
| EP | 1 690 564 A1 | 8/2006 |
| EP | 1 743 575 A2 | 1/2007 |
| EP | 1 820 464 A1 | 8/2007 |
| EP | 1 897 581 A2 | 3/2008 |
| EP | 2 000 789 A2 | 12/2008 |
| EP | 2 047 797 A2 | 4/2009 |
| EP | 2 127 604 A1 | 12/2009 |
| EP | 2 130 508 A2 | 12/2009 |
| EP | 2 172 240 A1 | 4/2010 |
| EP | 2 338 412 A1 | 6/2011 |
| JP | 2005-345215 A | 12/2005 |
| JP | 2006064465 | 3/2006 |
| WO | WO 95/10326 | 4/1995 |
| WO | WO 96/05768 | 2/1996 |
| WO | WO 97/29678 | 8/1997 |
| WO | WO 97/29709 | 8/1997 |
| WO | WO 97/29710 | 8/1997 |
| WO | WO 98/29032 | 7/1998 |
| WO | WO 03/020139 A2 | 3/2003 |
| WO | WO 2006/029563 A1 | 3/2006 |

| WO | WO 2006/086152 A2 | 8/2006 |
| WO | WO 2006/092563 A1 | 9/2006 |
| WO | WO 2007/025230 A2 | 3/2007 |
| WO | WO 2007/111182 A1 | 4/2007 |
| WO | WO 2007/050960 A2 | 5/2007 |
| WO | WO 2007/067938 A2 | 6/2007 |
| WO | WO 2007/082216 A1 | 7/2007 |
| WO | WO 2007/098494 A1 | 8/2007 |
| WO | WO 2009/078280 A1 | 6/2009 |
| WO | WO 2009/085470 A1 | 7/2009 |
| WO | WO 2009/147399 A1 | 12/2009 |
| WO | WO 2010/008975 A2 | 1/2010 |

OTHER PUBLICATIONS

Partial European Search Report for corresponding EP Application No. 11189326.9 mailed Feb. 15, 2012, 6 pages.

Extended European Search Report dated May 2, 2012 for European Patent Application No. 11189326.9 (20 pages).

Biter, W. J. et al., "Magnetic Wire Strain Sensor", $33^{rd}$ International SAMPE Technical Conference, Nov. 2001, vol. 33, pp. 12-23, Seattle, WA.

Biter, W, J. et al., "Magnetic Wire for Monitoring Strain in Composites", Sensors, Jun. 2001, www.sensormag.com, pp. 110-114.

Okumura, Y. et al., "A Systematic Analysis of In Vivo Contact Forces on Virtual Catheter Tip/Tissue Surface Contact during Cardiac Mapping and Intervention", *Journal of Cardiovascular Electrophysiology*, vol. 19, No. 6, Jun. 2008, pp. 632-640.

* cited by examiner

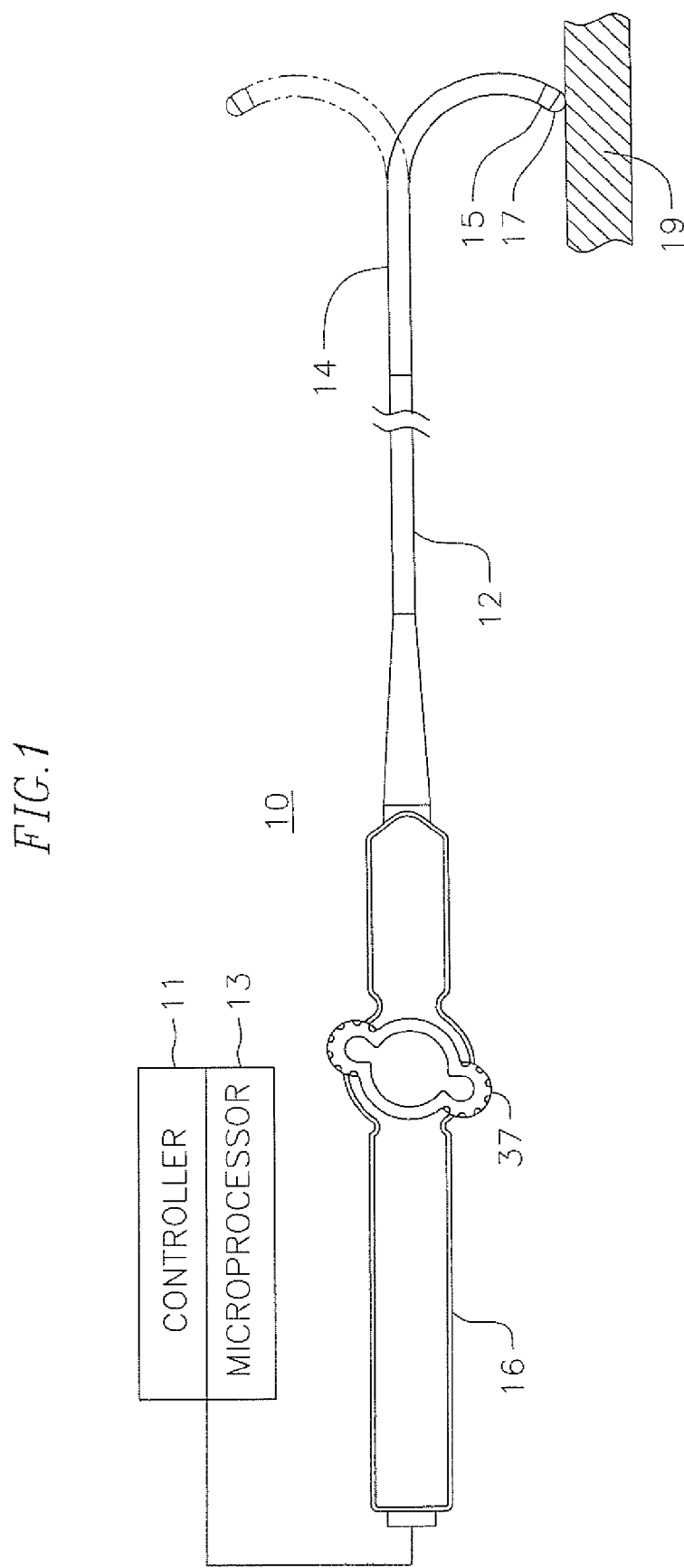

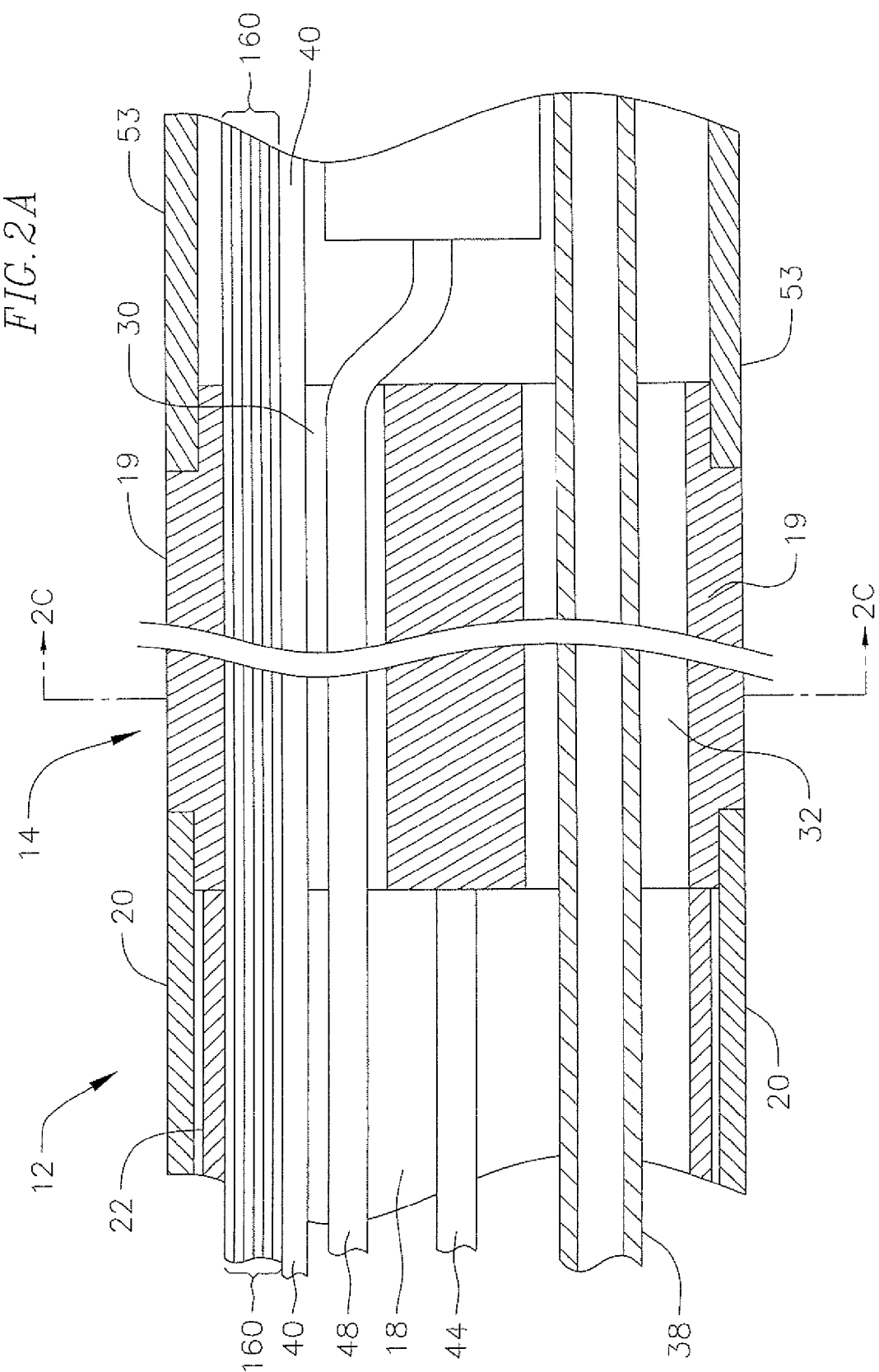

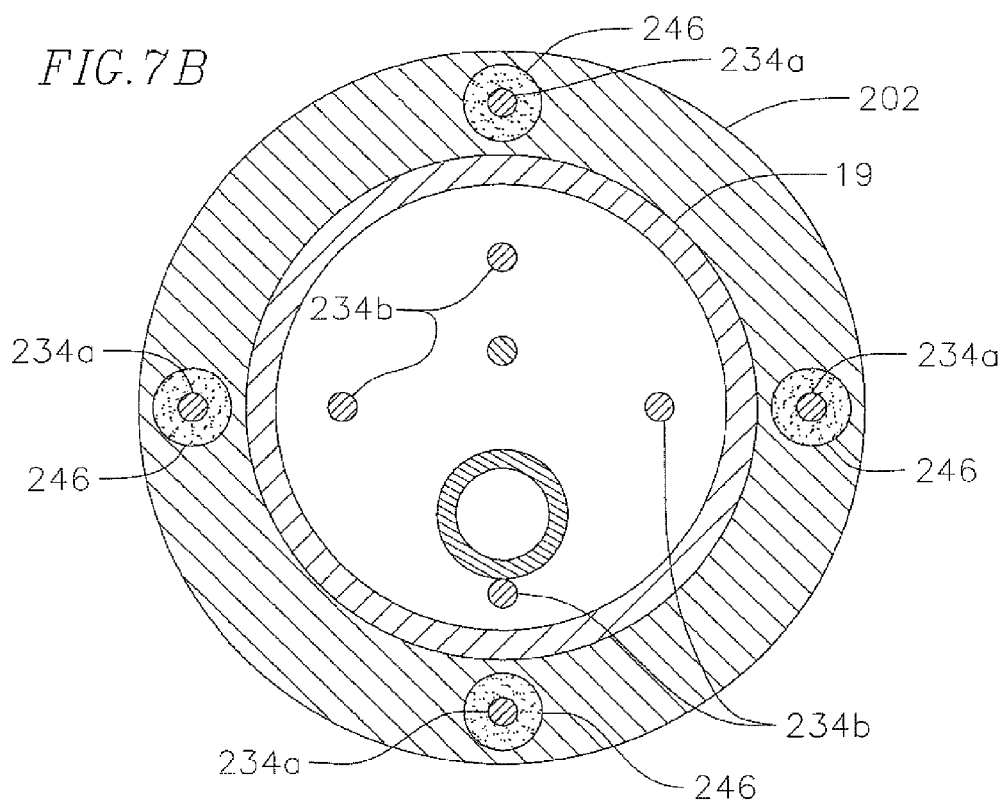
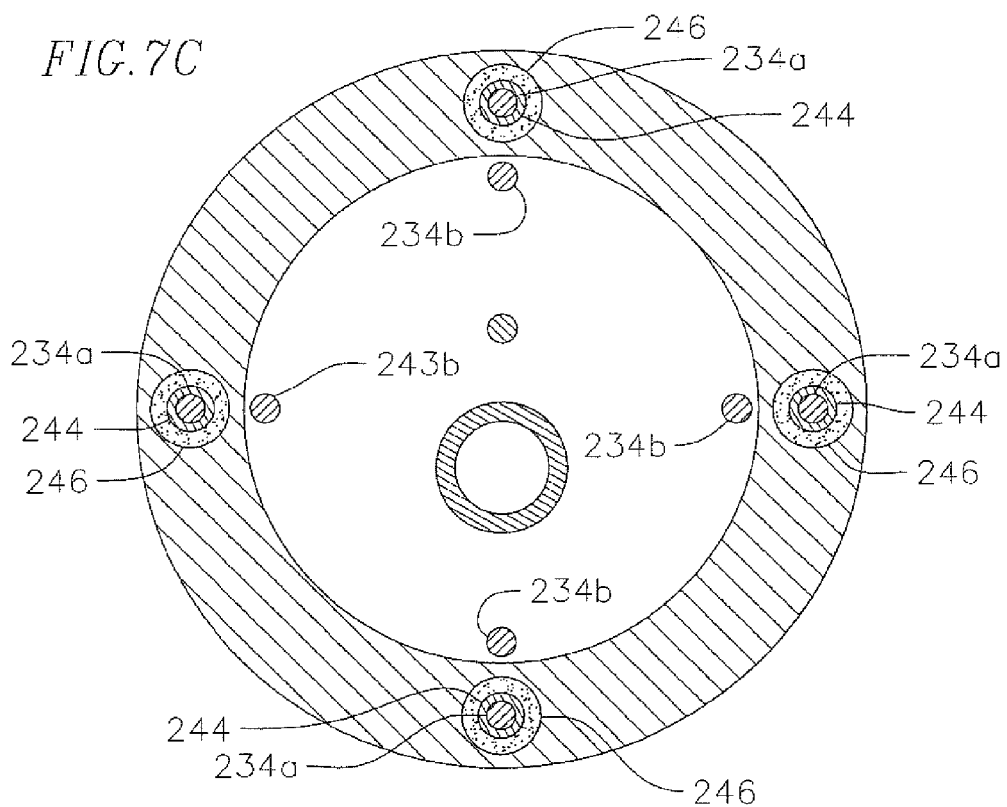

CATHETER HAVING A FORCE SENSING DISTAL TIP

FIELD OF INVENTION

The present invention relates to an electrophysiologic catheter useful for ablation and sensing electrical activity of heart tissue, in particular, an electrophysiologic catheter with contact force sensing capabilities at its distal end.

BACKGROUND OF INVENTION

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Diagnosis and treatment of cardiac arrythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Ablation and mapping involves contacting tissue wall with the tip electrode of the catheter. However, proper positioning of the tip electrode relative to tissue wall is not always possible. It is therefore desirable to provide catheters with contact force sensing at a distal tip. Recent studies have suggested that lesion depth may be dependent on contact force of the tip electrode against tissue wall during RF ablation.

Accordingly, it is desirable that a catheter be adapted for mapping and ablation with contact force sensing at the distal tip electrode. It is also desirable that such a catheter be equipped with tri-axial sensors for determining a three dimensional contact force vector acting upon the catheter tip. Since the catheter location is monitored using a magnetic based location sensor and the heart chamber walls are mapped in 3D, it is possible to determine the tip electrode contact area in relation to the heart wall and thus calculate the tip electrode contact pressure.

SUMMARY OF THE INVENTION

The present invention is directed to a mapping and ablation catheter with contact force sensing capabilities at a distal end. The catheter includes a catheter body, a deflectable section, and a tip distal section which has a tip electrode and an integrated contact force sensor for sensing a 3D contact force vector applied to the tip electrode. The contact force sensor has a body and at least one sensor with an electrical characteristic that is responsive to deformation of the body. The sensor is adapted to receive an electrical current and to output an electrical signal indicative of a change in the electrical characteristic. In one embodiment, the sensor is a strain gage responsive to tension and compression of at least a portion of the body of the force sensor and the electrical characteristic of the strain gage being monitored is electrical resistivity. In another embodiment, the sensor is responsive to strain and stress of at least a portion of the body, and the electrical characteristic being monitored is inductance or hysteresis loss.

In a more detailed embodiment, the catheter of the present invention includes a catheter body, a deflectable intermediate section and a tip section with a tip electrode and a contact force sensor susceptible to material strains produced by bending moments and both tension and compression forces applied to the catheter tip electrode. The contact force sensor has a cup shaped body, a plurality of radial spokes, an axial beam member, and at least one strain gage mounted on one of the spokes. The spokes converge at a centered hub on the body from which the beam member extends and is connected to the tip electrode so that an applied contact force vector is transmitted from the tip electrode to the beam member which deforms and strains the body of the force sensor. A gap is provided along the longitudinal axis between the tip electrode and body of the force sensor so that a moment load can be imported to the beam from a force vector acting on the tip electrode. Each spoke of the force sensor may have more than one strain gage mounted thereon, for example, two strain gages on opposite surfaces of the spoke mounted in symmetry of each other. In this symmetrical configuration, each strain gage cancels the other's temperature effects when a half bridge electrical configuration is used for strain measurement and it also increases and doubles the change in the resistance output (resistance measurement sensitivity) per unit strain input to the body.

In another detailed embodiment, the catheter of the present invention has a catheter body, a deflectable immediate section, a tip section with a tip electrode and a contact force sensor susceptible to strain and stress. The contact force sensor has a cylindrical body and at least one strain sensor wire. The wire is electrically conductive and has a segment that is surrounded by a strain-sensitive magnetic film. The segment and magnetic film are pre-stressed and embedded in the body. The tip electrode has a proximal stem and the cylindrical body has a distal end which is trepanned to receive the proximal stem of the tip electrode. The force sensor can have a plurality of strain sensor wires, for example, at least three strain sensor wires, each having a segment that is surrounded by a magnetic film, where each of the segments with its magnetic film is pre-stressed and embedded in the body. Each of the strain sensor wires is positioned equi-distanced from each other in a radial pattern around the longitudinal axis of the force sensor for radial symmetry.

BRIEF DESCRIPTION OF THE DRAWINGS

These and other features and advantages of the present invention will be better understood by reference to the following detailed description when considered in conjunction with the accompanying drawings wherein:

FIG. 1 is a top plan view of one embodiment of the catheter of the present invention.

FIG. 2a is a side cross-sectional view of an embodiment of a junction of a catheter body and an intermediate section, and a junction of the intermediate section and a connective housing, taken along a first diameter.

FIG. 7B is an end cross-sectional view of the embodiment of the distal tip section of FIG. 7, taken along line B-B.

FIG. 7C is an end cross-sectional view of the embodiment of the distal tip section of FIG. 7, taken along line C-C.

DETAILED DESCRIPTION OF THE INVENTION

Figure 2B:
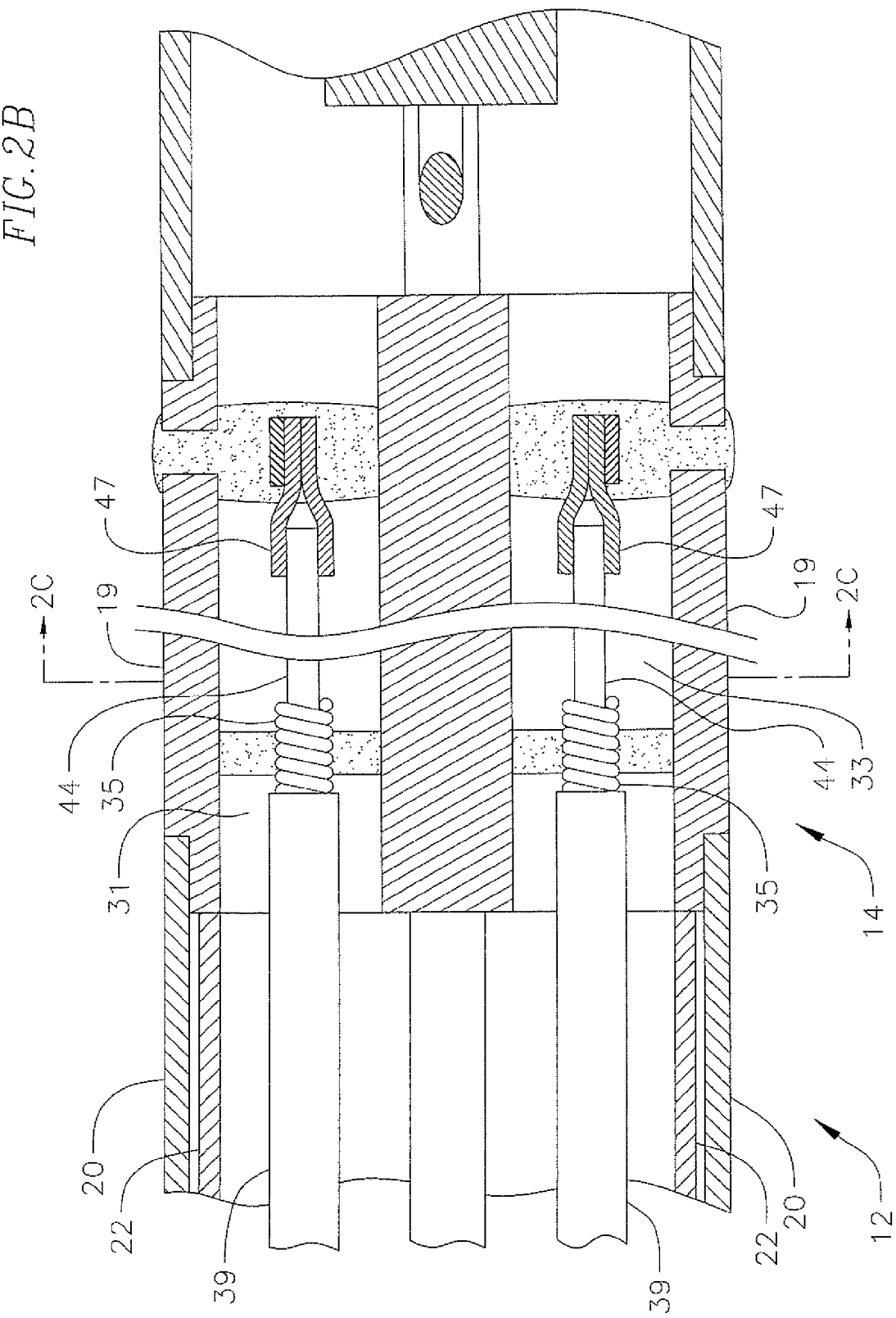
FIG. 2b is a side cross-sectional view of the embodiment of the junctions of FIG. 2a, taken along a second diameter generally perpendicular to the first diameter.

FIG. 1 illustrates an embodiment of a catheter 10 with force-sensing capabilities at a distal tip. The catheter has an elongated catheter body 12 with proximal and distal ends, an intermediate deflectable section 14 at the distal end of the catheter body 12, and a distal section 15 adapted for mapping, ablation and detecting forces applied to a tip electrode 17 such as when the tip electrode is in contact with tissue wall 19. The catheter also includes a control handle 16 at the proximal end of the catheter body 12 for controlling bi-directional deflection of the intermediate section 14. The control handle 16 may further serve as a conduit to a controller 11 adapted to send, receive and process electrical input and output signals to and from the distal section 15 for mapping, ablation and/or force sensing, such as by means of a microprocessor 13 applying program algorithms with force sensing solutions. In accordance with the present invention, such signals include signals from a tri-axial force sensor housed in the distal section 15 that detects and measures contact forces on the tip electrode, whereby the controller and microprocessor are adapted to processes such signals in computing a contact force vector.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate wires, cables, tubings and the like. If desired, the inner surface of the outer wall 20 is lined with a stiffening tube 22 to provide improved torsional stability. In a disclosed embodiment, the catheter has an outer wall 20 with an outer diameter of from about 0.090 inch to about 0.100 inch and an inner diameter of from about 0.061 inch to about 0.065 inch. Distal ends of the stiffening tube 22 and the outer wall 20 are fixedly attached to each other by adhesive bonds therebetween near the distal end and proximal ends of the catheter body 12

Components that extend between the control handle 16 and the deflectable section 14 pass through the central lumen 18 of the catheter body 12. These components include lead wire(s) 40 for the tip electrode 17 and any ring electrodes of the tip section 15, main lead wires 160 for a force sensor in the tip section, an irrigation tubing 38 for delivering fluids to the tip section 15, a cable 48 for an electromagnetic position location sensor, and/or a pair of puller wires 44 for bidirectional deflection of the intermediate section 14.

Figure 2C:
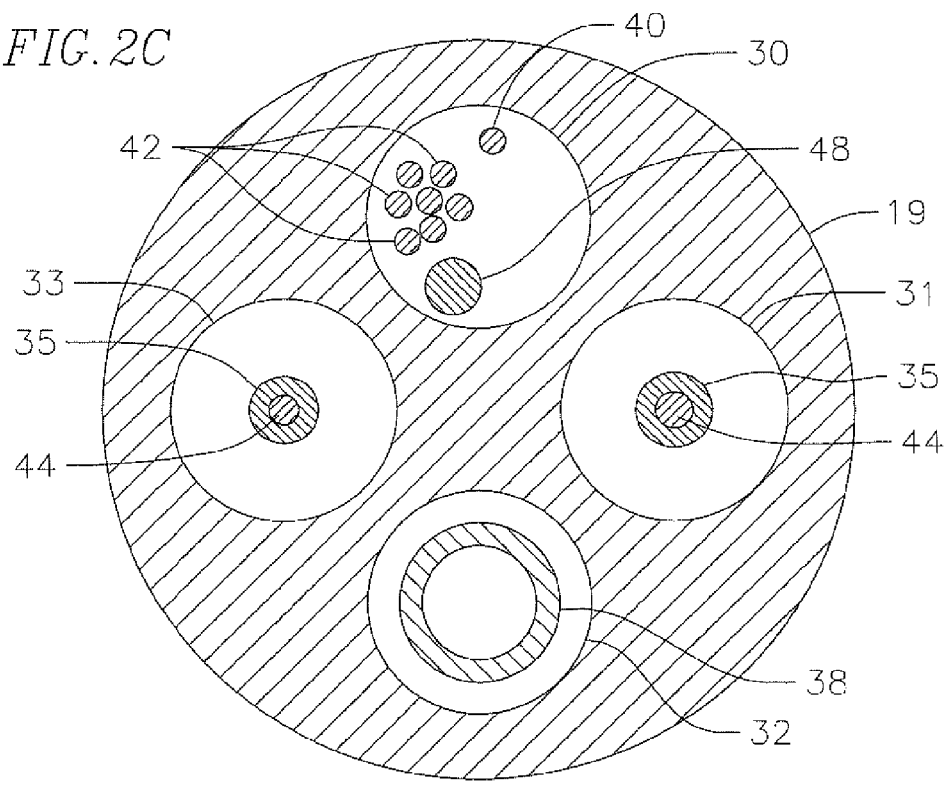
FIG. 2c is an end cross-sectional view of the embodiment of FIGS. 2a and 2b, taken alone line C-C.

Also illustrated in FIGS. 2A, 2B and 2C is an embodiment of the deflectable intermediate section 14 which comprises a shorter section of tubing 19. The tubing also has a braided mesh construction but with multiple off-axis lumens, for example first, second, third and fourth lumens 30, 31, 32 and 33. In the illustrated embodiment, each of diametrically opposing second and fourth lumens 31 and 33 carries one puller wire 44 for bi-directional deflection. The first lumen 30 carries the lead wires 40, the main lead wires 160, and the sensor cable 48. The third lumen 32 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane or PEBAX with an embedded mesh of braided stainless steel or the like. The size of each lumen is not critical, but is sufficient to house the respective components extending therethrough.

A means for attaching the catheter body 12 to the tubing 19 of the intermediate section 14 is illustrated in FIGS. 2A and 2B. The proximal end of the intermediate section 14 comprises an outer circumferential notch that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 44 is preferably coated with Teflon®. The puller wires 44 can be made of any suitable metal, such as stainless steel or Nitinol and the Teflon coating imparts lubricity to the puller wire. The puller wire preferably has a diameter ranging from about 0.006 to about 0.010 inch. As shown in FIGS. 2B and 2C, a portion of each puller wire 44 in the catheter body 12 passes through a compression coil 35 in surrounding relation to its puller wire 44. The compression coil 35 extends from the proximal end of the catheter body 12 to the proximal end of the intermediate section 14. The compression coil 35 is made of any suitable metal, preferably stainless steel, and is tightly wound on itself to provide flexibility, i.e., bending, but to resist compression. The inner diameter of the compression coil is preferably slightly larger than the diameter of the puller wire 44. Within the catheter body 12, the outer surface of the compression coil 35 is also covered by a flexible, non-conductive sheath 39, e.g., made of polyimide tubing.

Proximal ends of the puller wires 44 are anchored in the control handle 16. Distal ends of the puller wires are anchored near the distal end of the intermediate section 14 as shown in FIG. 2B. The distal end of each puller wire is provided with a T-shaped anchor 47 that includes a short piece of tubular stainless steel, e.g., hypodermic stock, that is fitted over and crimped onto the distal end of the puller wire. The tubular stainless steel is fixed, e.g., by welding, to a cross-piece formed of stainless steel ribbon or the like. The cross-piece is fixedly secured to the outer wall of the tubing 19 to anchor the distal end of each puller wire. A first puller wire passes through the second lumen 31 and a second puller wire passes through the fourth lumen 33 of the deflectable intermediate section 14. Separate and independent longitudinal movement of the deflection wires 44 relative to the catheter body 12, which results in deflection of the intermediate section 14 and hence steering of the tip section 15 is accomplished by suitable manipulation of a deflection member 37 (FIG. 1).

Figure 3C:
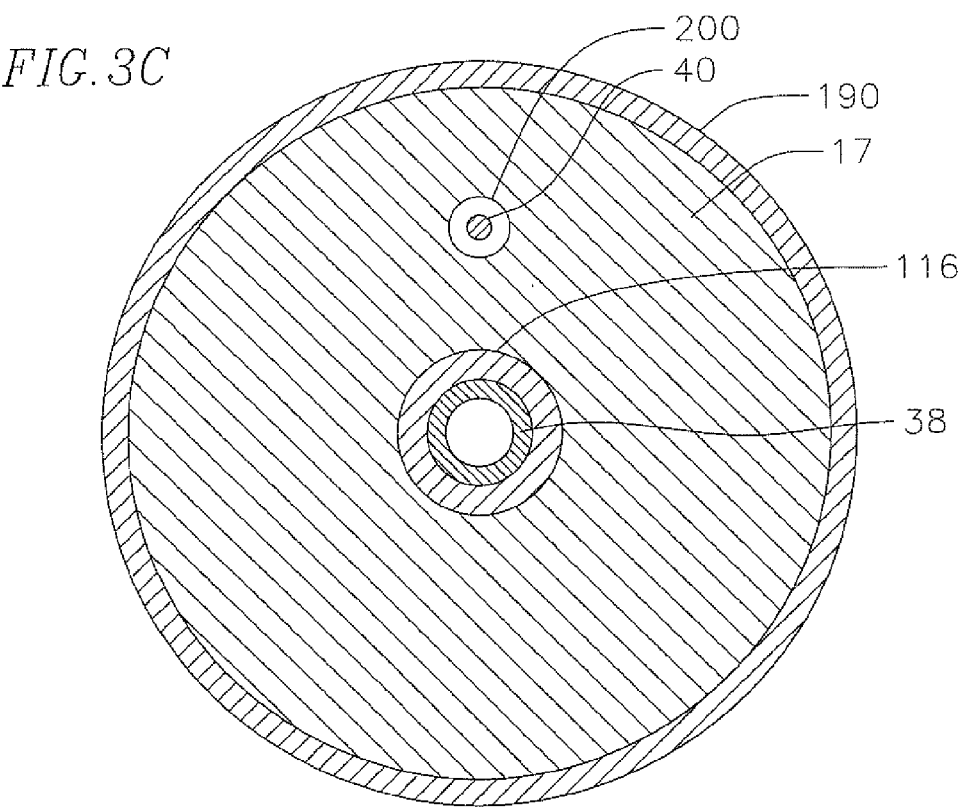
FIG. 3c is an end cross-sectional view of the embodiment of the distal tip section of FIG. 3, taken along line C-C.
Figure 3:
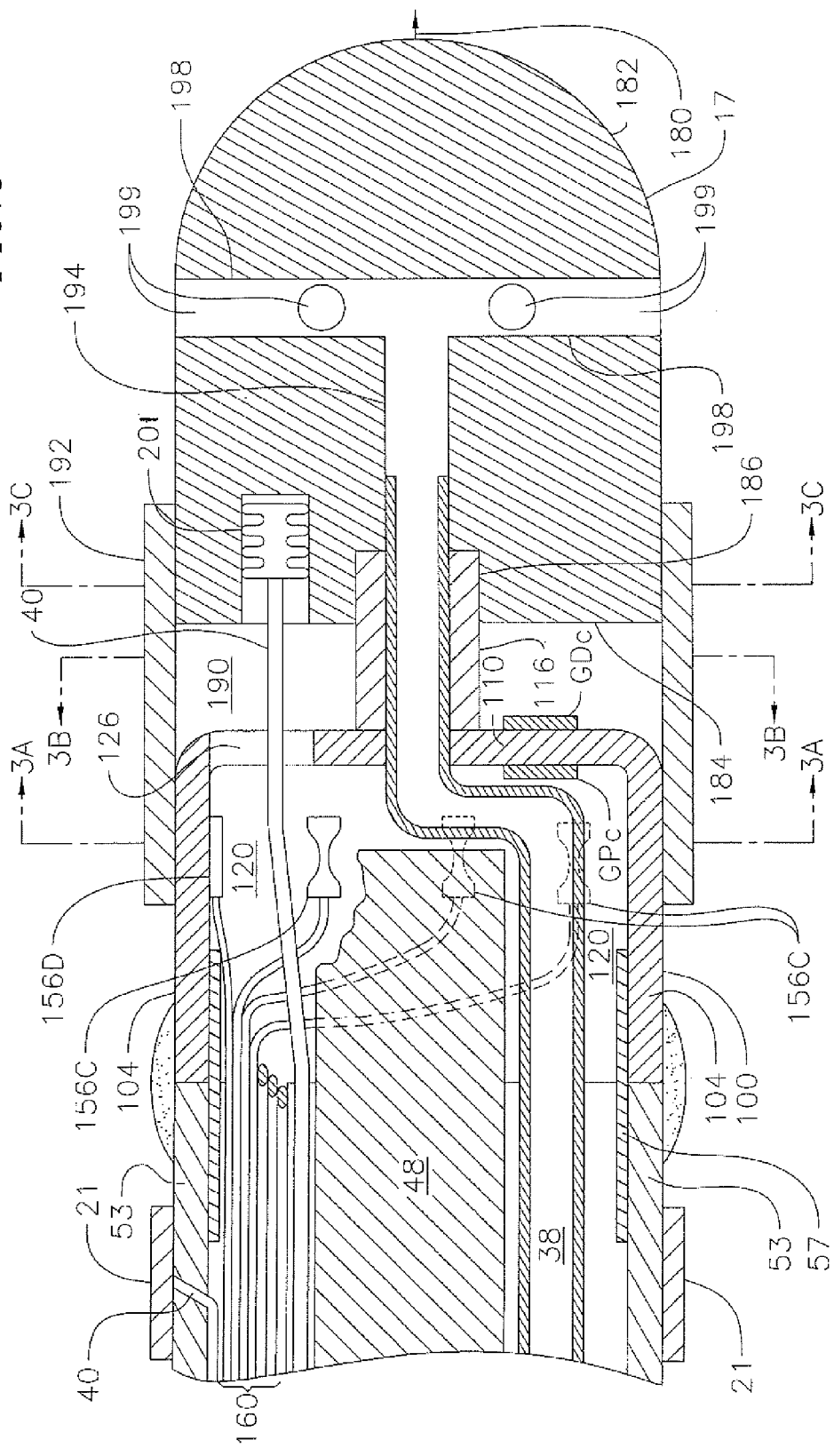
FIG. 3 is a side cross-sectional view of an embodiment of a distal tip section of the catheter of the present invention, including a tip electrode and a contact force sensor susceptible to tension and compression.
Figure 4:
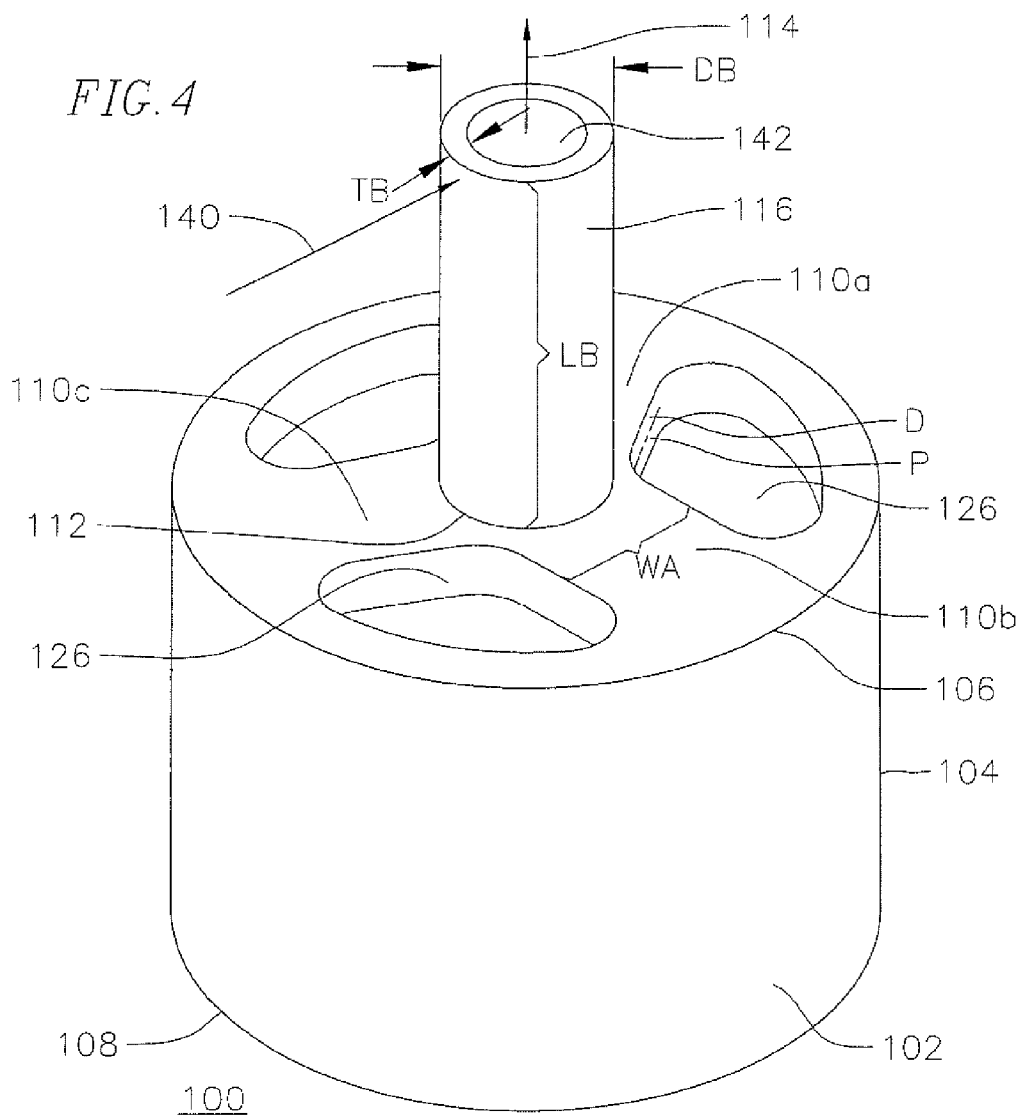
FIG. 4 is a perspective front view of the force sensor of FIG. 3.
Figure 5:
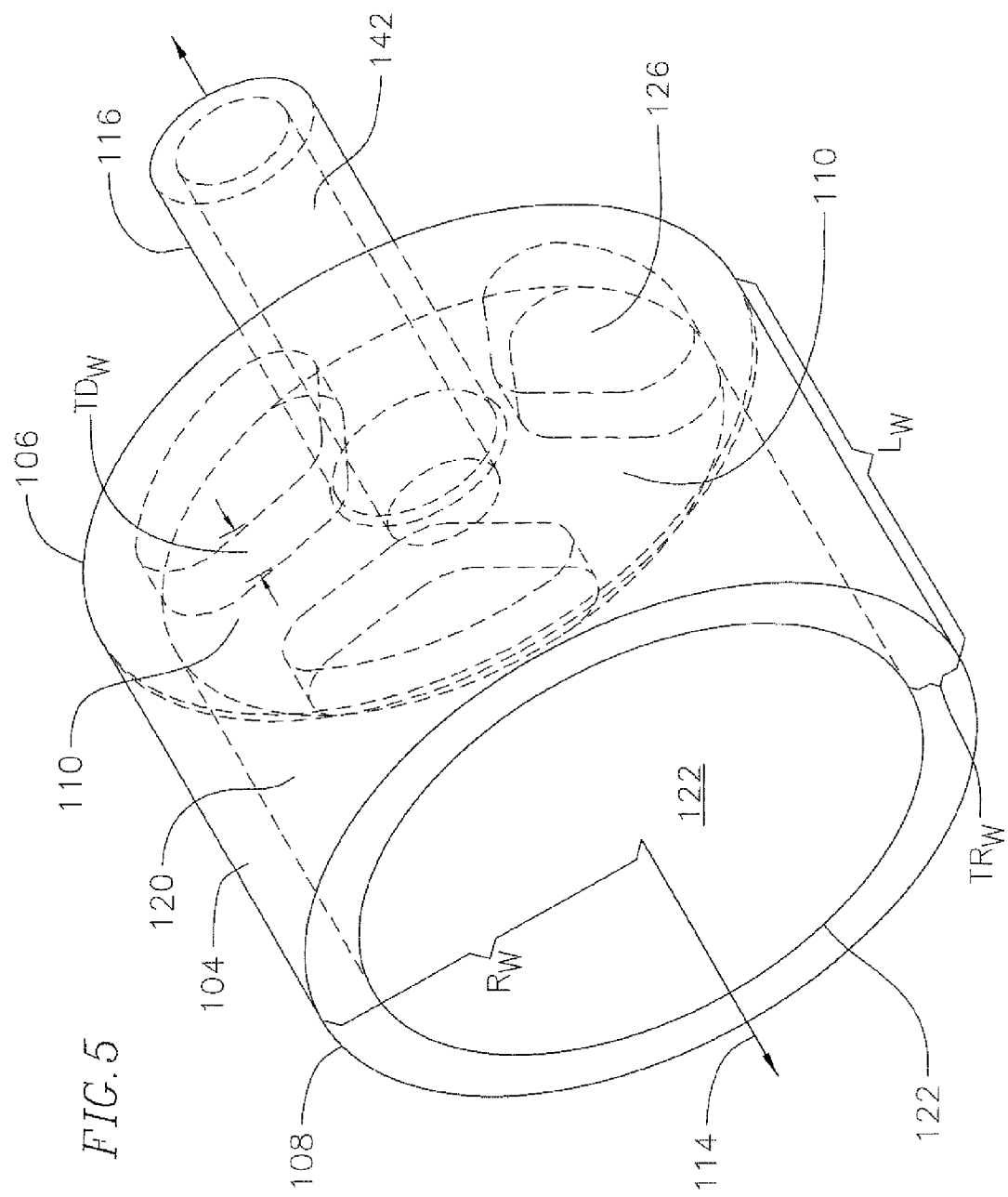
FIG. 5 is a perspective rear view of the force sensor of FIG. 3.

At the distal end of the intermediate section 14 is the tip section 15 that includes the tip electrode 17 and a force sensor 100. With reference to FIGS. 3, 4 and 5, the force sensor has a "cup" shape body 102, with a generally cylindrical wall 104 with a distal end 106 and a proximal end 108, a plurality of spaced-apart radial arms or spokes 110 that lie generally within a transverse plane at the distal end 106. It is understood by one of ordinary skill in the art that the arms need not lie on the transverse plane and may be curved so long as they are radially symmetrical. The arms 110 converge centrally at a hub 112 on a longitudinal axis 114 of the force sensor. A distal linear member 116 extends distally from the hub 112 along the longitudinal axis 114 of the force sensor. The cylindrical wall 104 and the arms 110 have generally the same thickness, and each arm has a common generally uniform width between the annular wall and the hub. The cylindrical wall 104 defines a hollow interior 120 between the proximal end 108 and the distal end 106. At the proximal end 108, the wall 104 circumscribes an opening 122 into the hollow interior 120. At the distal end, the arms 110 define between them generally triangular or wedge-shaped apertures 126 allowing access and passage into the hollow interior 120 from or to the distal direction.

In the illustrated embodiment, the linear member 116 is a hollow cylindrically shaped beam with a circular cross-section, although it is understood that the beam can have any cross-sectional shape that is symmetrical about the longitudinal axis 114 and any planar sections are in alignment with the arms 110. Because of the size of the force sensor 100, the shape of the beam depends largely on available fabrication techniques. Extending distally with its proximal end fixedly mounted or otherwise connected to each of the arms 110 and the hub 112, the beam 116 is susceptible to compression-tension and/or moment load along its length which is transferred to the arms 110. With reference to FIG. 4, where a force is applied to the beam 116 in the direction of arrow 140, the stress/strain experienced by the arm 110a creates compression in the distal half D of the arm and tension in the proximal half P of the arm. It is understood by one of ordinary skill in the art that by measuring the compression and tension in each of the arms, any force with radial and/or axial components can be measured to determine a tri-axial force vector in a 3-dimensional coordinate system. Moreover, since the catheter tip location is monitored using a magnetic based location sensor and the heart chamber walls are mapped in 3D, it is possible to determine the tip electrode contact area in relation to the heart wall and thus calculate additional parameters, such as a tip electrode contact pressure. Such a vector and/or parameters are useful in determining whether the tip electrode is properly positioned against the tissue wall, as insufficient contact force may result in inadequate lesion formation (lesion depth corresponds to contact force) and excessive contact force may result in perforation of tissue wall.

In the illustrated embodiment, the beam 116 has a hollow interior 142 and thus can function as a central fluid port through which irrigation or other fluids, such as saline or heparin, can be delivered to the tip electrode to cool tissue, reduce coagulation and/or facilitate the formation of deeper lesions with increased RF energy input. Moreover, lead wires, safety wires, etc., can pass through the apertures 126 between the arms 110. In the illustrated embodiment, there are at least three radial arms 110a, 110b, 110c, although it is understood by one of ordinary skill in the art that the plurality can range between about two and ten, with the limitation residing largely in fabrication techniques.

The force sensor 100 is radially symmetrical about its longitudinal axis 114, with the arms 110 being of the same shape and size and being equi-distanced from each other radially about the longitudinal axis. Where there are three arms, the arms are centered at about 0 degree, 120 degree and 240 degree about the longitudinal axis, with the width of each arm spanning about 30 degrees at junction of the arms and the annular wall. The force sensor can be made of any suitable material(s) that have sufficiently low thermal expansion coefficients. Suitable materials include stainless steel and titanium, e.g., 17-4 or 15-5 stainless steel, and 6AL-4V titanium. In that regard, preferred materials for the force sensor, having optimum static error band which is comprised of non-linearity, non-repeatability and hysteresis, include metals with low hysteresis and low thermal expansion which as 17-4PH or titanium 6AL4V. In constructing the force sensor, it is preferable to avoid using different materials that have varied thermal expansion coefficients.

The "cup" shape of the force sensor body 102 can be formed utilizing suitable methods, including drawn cup forming methods. The arms 110 can be formed utilizing suitable methods, including laser cut, punched or milled. The beam 116 can be attached to the hub using any suitable methods, including either spin welding, brazing or laser welding. The force sensor can also be fabricated from bar stock (single piece) on a Swiss type CNC lathe.

In the embodiment of FIGS. 4 and 5, the wall 204 has an outer radius RW of about 0.046 inches, a length LW of about 0.069 inches and a radial thickness TRW of about 0.008 inches and a distal thickness TDW of about 0.007 inches. The beam 116 has an outer diameter DB of about 0.030 inches, a length LB of about 0.058 inches and a thickness TB of about 0.004 inches (see FIG. 4). Each arm has a width WA of about 0.024 inches.

Figure 3A:
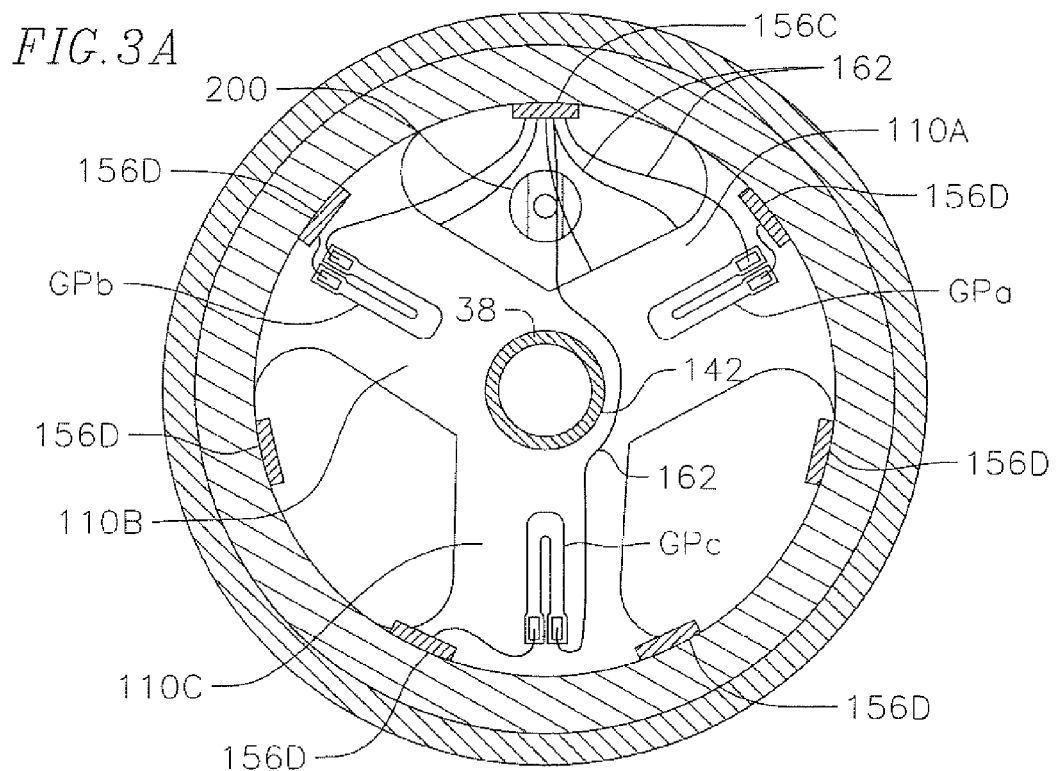
FIG. 3a is an end cross-sectional view of the embodiment of the distal tip section of FIG. 3, taken along line A-A.
Figure 3B:
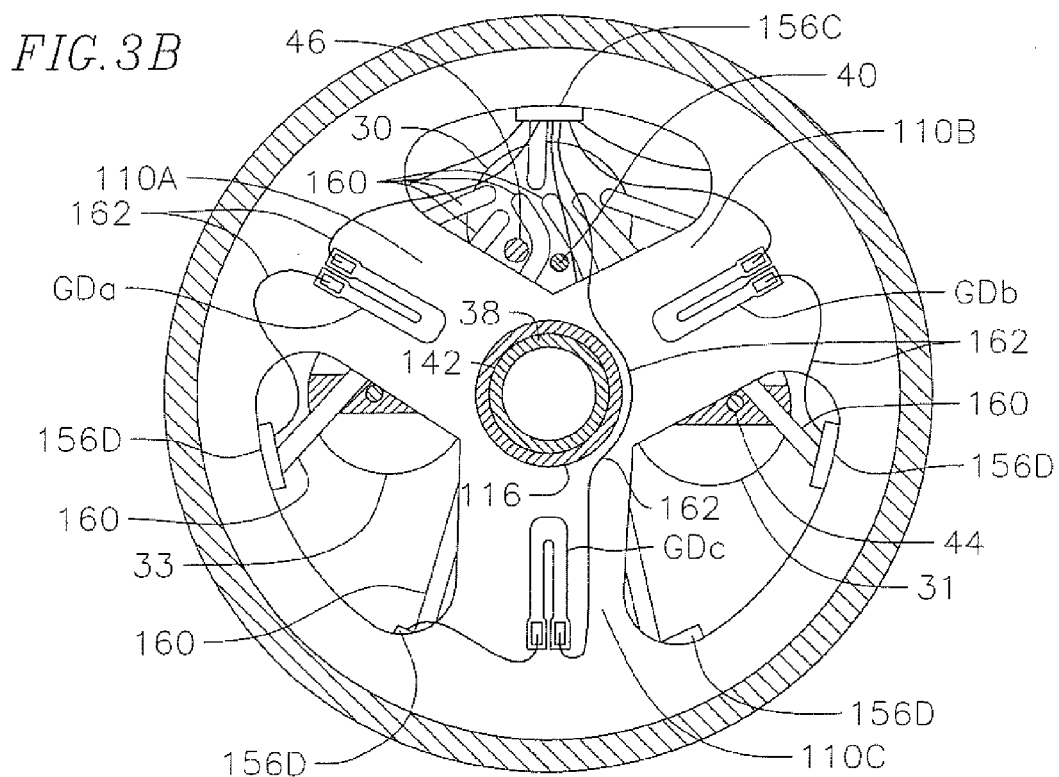
FIG. 3b is an end cross-sectional view of the embodiment of the distal tip section of FIG. 3, taken along line B-B.

As shown in FIGS. 3A and 3B, each arm or spoke 110 is advantageously provided with at least one silicon semiconductor strain gauge or strain sensor ("sensor" and "gage" used interchangeably herein) on a distal surface and/or a proximal surface of the arm 110. In the illustrated embodiment, one strain gage is mounted on each distal and proximal surface of each arm for a total of three proximal strain gages GPa, GPb and GPc and three distal strain gages GDa, GDb, GDc. Each strain gage is responsive to tension or compression experienced by its respective proximal or distal half of the arm on which the strain gage is mounted. The six U-shaped strain gages forming three pairs (GPa/GDa), (GPb/GDb), (GPc/GDc), each pair being of a distal gage and a proximal gage on the same arm, are symmetrically mounted on the arms by an adhesive such as epoxy.

As understood by one of ordinary skill in the art, semiconductor strain gages are devices which vary in electrical resistance as strain is applied to them. This property makes them very useful in measuring extremely small amounts of force induced material strain with accuracy and precision. Gages made from semiconductor materials have advantages over more conventional types of strain gage. These include the ability to measure wide range of material strain (tested up to 3× over range), increased "sensitivity" (strains can be measured reliably to 0.1 micro-inch resolution) and decreased size. Semiconductor strain gages can vary in shape, including bar-shaped, U-shaped and M-shaped, such as those manufactured by Micron Instruments of Simi Valley, Calif. The strain gages are intended to provide a calculated theoretical force resolution of ±0.1 grams. Utilizing a 500 micro-strain full-scale operational range for the strain gages, the sensor provides a tip electrode force vector measurement span ranging between 0-150 grams and force over limit (create permanent deformation in body by exceeding material yield strength) safety factor of about 750 grams. As understood by one of ordinary skill in the art, the strain gage can be customized to compensate for various parameters, including the force sensor's non-linear radial strain line, strain gage placement accuracy on the force sensor and force sensor body manufacturing tolerances.

While each pair of strain gage on an arm can also function as a single temperature sensor therefor temperature can also be monitored at their locations on each arm, the pair of gages, one on each side of an arm, advantageously cancel out material temperature effects. When there is a change in temperature of the material of the arm, the material expands or contracts an amount (on the order of, for example, micro-inches per inch). Thus, having a gage on each side of the arm advantageously cancels out temperature effects due to material coefficient of expansion.

Figure 6:
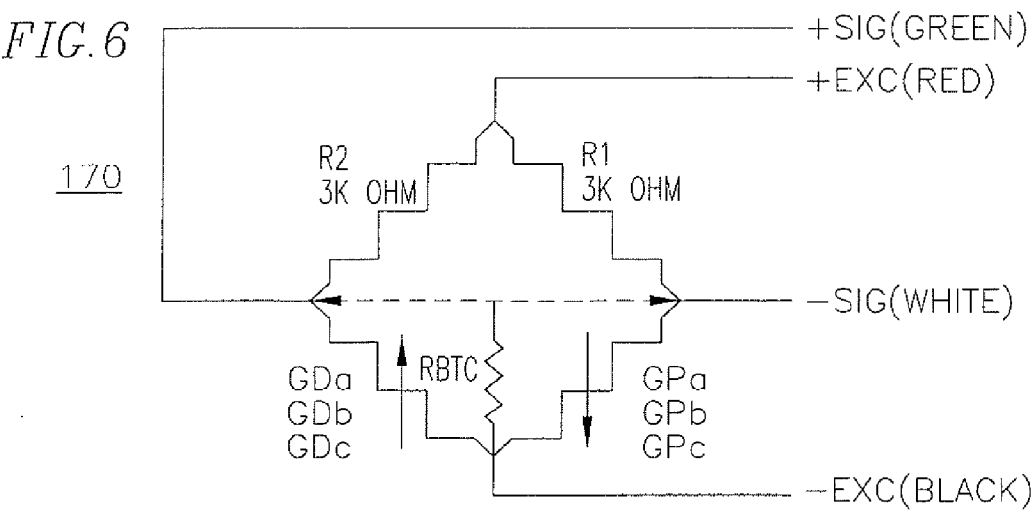
FIG. 6 is a schematic view of an embodiment of a bridge circuit adapted for use with the force sensor of FIG. 3.

Mounted on an inner circumference of the wall 104, in equi-distance from each other radially, are a plurality of bonded terminals (solder tabs) 156 adapted for use in a strain gage circuit. In one embodiment, the terminals are manufactured from about 0.14 thick copper clad epoxy glass which insures electrical insulation while remaining flexible, strong and capable of high temperatures up to about 275° F. The terminals are employed between larger diameter main lead wires (e.g., copper wires) 160 and smaller delicate strain gage leads (e.g., 24K gold wires) 162, the latter of which each strain gage has a first strain gage lead and a second strain gage lead. In the illustrated embodiment, there is one common terminal 156C and six dedicated terminals 156D. The common terminal 156C receives a first gage lead 162 from each strain gage, and each of the six dedicated terminals 156D receives a second gage lead 162 from each of the strain gages. Of the seven main lead wires 160, one main lead wire is connected at its distal end to the common terminal 156C, and each of the remaining six main lead wires is to a different one of the six dedicated terminals 156D. The main lead wires 160 are coupled at their proximal end to a Wheatstone bridge circuit 170 as illustrated in FIG. 6. In the illustrated embodiment, the circuit includes three half bridges (one half bridge for each pair of gages GPa/GDa, GPb/GDb, GPc/GDc), which effectively double the gage output and cancel the material temperature effects of each arm, and the circuit is balanced with bridge completion and sensitivity compensating resisters R1 and R2 (e.g., 3000 ohm) with a bridge excitation voltage (e.g., 5.0 VDC). A resistor balance temperature compensating (RBTC) may be required to further balance the bridge. Balance temperature compensation is the change in the bridge output voltage with respect to temperature with no load. For perfect balance, temperature compensation should be zero. A positive balance temperature compensation is defined as the bridge output voltage change going more positive with increasing temperature under no load when the bridge is properly excited with a voltage. Negative temperature compensation is a decreasing voltage output with increasing temperature. This occurs when one gage is changing resistance faster than the other. To reduce the change to zero, it is possible to short the gage changing faster with a RBTC as shown in FIG. 6. Applying the RBTC across the bridge can unbalance the bridge and the resulting unbalance can be readjusted by changing one of the bridge completion resistors R1 or R2.

As understood by one of ordinary skill in the art, a bridge excitation voltage is dependent on self heating of the strain gages and thus overall wattage input into the gage is predetermined. Input to the circuit can be DC, AC sine wave or square wave form as long as the overall wattage is maintained below a threshold to prevent gage self heating. For example, 5V DC into a 500 ohm strain gage is not expected to produce self heating but 10V DC into the same strain gage can create heating issues. To increase the sensitivity of the gage strain measurement, the gage can be pulse driven (square waveform with low duty cycle) at a higher voltage (e.g., 100V DC) for a 1% duty cycle to limit the average wattage into the gage. The gages are adapted to measure the strain of the spoke 110 that they are bonded to by providing a change in resistance with respect to applied strain. The change in resistance in turn changes the voltage output of the bridge (E=I×R) thus a high input voltage to the gage increases their output sensitivity. As understood by one of ordinary skill in the art, the strain gages may require compensation resistors depending on the type of strain gage being used.

The distal section 15 also includes a short piece of connection tubing 53 between the force sensor 100 and the deflectable intermediate section 14. In the illustrated embodiment of FIG. 3, the connection tubing 53 has a single lumen which allows passage of the tip electrode lead wire 40 and the irrigation tubing 38 into the tip electrode 17. The tubing 53 also houses the electromagnetic position sensor 48 whose cable 46 extends proximally therefrom through the tubing. The tubing 53 also allows passage of the main lead wires 160 from the bonded terminals 156 inside the force sensor 100. The single lumen of the connection tubing 53 allows these components to reorient themselves as needed from their respective lumens in the intermediate section 14 toward their location within the tip electrode 17.

It is understood that an objective of the present invention is to provide in the distal tip section 15 a compliant section that deforms (strains), such as the force sensor 100, and a rigid non-compliant section that is rigid and resists all deformation, such as a distal stiffening tube 57, so the compliant section absorbs almost all of the strain energy from the force vector acting on tip electrode 17. The force sensor 100 and the distal stiffening tube 57 should be made from the same material, or at least materials with similar thermal expansion coefficients, to prevent thermal hysteresis (strains caused by different material rates of thermal expansion and contraction) due to different coefficients of expansion of each material. In one embodiment, the distal stiffening tube is a thin walled rigid tube 57 with dimensions of 0.003-0.006 inches thick by 0.125-0.250 inches long. The tube is attached, for example, by press fit or adhesive bonded, to the inner or outer diameter of the proximal end of the force sensor 100. In the embodiment illustrated in FIG. 3, the tube 57 is attached to the inner diameter of the force sensor 100. Hole(s) perpendicular to the longitudinal axis of the tube 57 can be formed so wiring to a ring electrode is facilitated.

As shown in FIG. 3, the tip electrode 17 defines a longitudinal axis 180 aligned with the longitudinal axis 114 of the force sensor. The tip electrode 17 has a dome-shaped atraumatic distal end 182 and a proximal end 184 having a generally planar surface in which a centered hole 186 is formed for receiving the beam 116 of the force sensor. The hole 186 has a depth that is less than the length LB of the beam so that a gap or space 190 exists between the tip electrode 17 and the body 102 and arms 110 of the force sensor. The gap 190 is intended to allow the tip electrode more freedom and movement for a greater torque at the distal end of the beam 116 thus allowing for better sensing of an applied force on the tip electrode in three dimensions. A thin, fluid-tight, flexible and elastic short section of tubing or a sealant 192 extends between the tip electrode and the body of the force sensor to help retain the tip electrode 17 on the beam 116 and keep the gap 190 clear of debris. Coaxial with the hole 180 is an irrigation passage 194 with radial transverse branches 198 to allow fluid delivered by the irrigation tubing 38 to exit to outside of the tip electrode via a plurality of radial ports 199.

The proximal end of the tip electrode 17 also includes a blind hole 201 in which the tip electrode lead wire 40 is anchored. The tip electrode lead wire 40 passes to the tip electrode 17 through one of the apertures 126 in the force sensor 100. As shown in FIG. 2A, the tip electrode lead wire passes through the first lumen 30 of the intermediate section 14, and the central lumen 18 of the catheter body 12 before reaching the control handle 16. The main lead wires 160 for the sensor gages also pass through the first lumen 30 of the intermediate section 14, and the central lumen 18 of the catheter body 12 before reaching the control handle 16 where they are connected to the bridge circuit 170.

The catheter distal tip section can include ring electrode(s) 21 which are mounted on the connection tubing 53 bridging the force sensor 100 and the distal end of the tubing 19 of the intermediate section, as shown in FIG. 3. The ring electrode 21 can be made of any suitable solid conductive material, such as platinum or gold, preferably a combination of platinum and iridium. The ring electrodes can be mounted onto the connection tubing 53 with glue or the like. Alternatively, the ring electrodes can be formed by coating the tubing 53 with an electrically conducting material, like platinum, gold and/or iridium. The coating can be applied using sputtering, ion beam deposition or an equivalent technique. The number of the ring electrodes on the tubing 53 can vary as desired. The rings may be monopolar or bi-polar. Each ring electrode is connected to a respective lead wire 40 which can pass through the first lumen 30 of the intermediate section 14 and the central lumen 18 of the catheter shaft 12. It is understood that insulating or protective sheaths can be provided for any of the wires and cables as needed throughout the catheter, including the catheter body 12 and/or the intermediate section.

An alternate embodiment of a catheter of the present invention is illustrated in FIGS. 7, 7A, 7B and 7C, in which similar elements are described with the same reference numbers. A catheter incorporates in the distal tip section 15 a force sensor 200 that includes a hollow cylindrical body or housing 202 and a plurality of embedded strain sensing tensile members 204 to monitor strain of the body 202 in sensing a three dimensional force vector applied to the electrode tip 17. With reference to FIG. 8, the body has a wall 206 with a circular cross section, a proximal end 208, and a trepanned or outer distal end 209 with an inner distal end 210. An outer length extends between the proximal end 208 and the outer distal end 209. An inner length extends between the proximal end 208 and the inner distal end 210. Between the proximal end and the inner distal end, the wall has a uniform thickness T. The wall has an outer circumferential surface 212, and an inner circumferential surface 214 defining an interior space 216. The wall is formed with a plurality of axial passages or through holes 218 arranged in equi-distance from each other radially around a longitudinal axis 220. Each axial passage 218 spans the inner length and defines a respective opening 222 in the proximal end 208 and the inner distal end 210.

Figure 7:
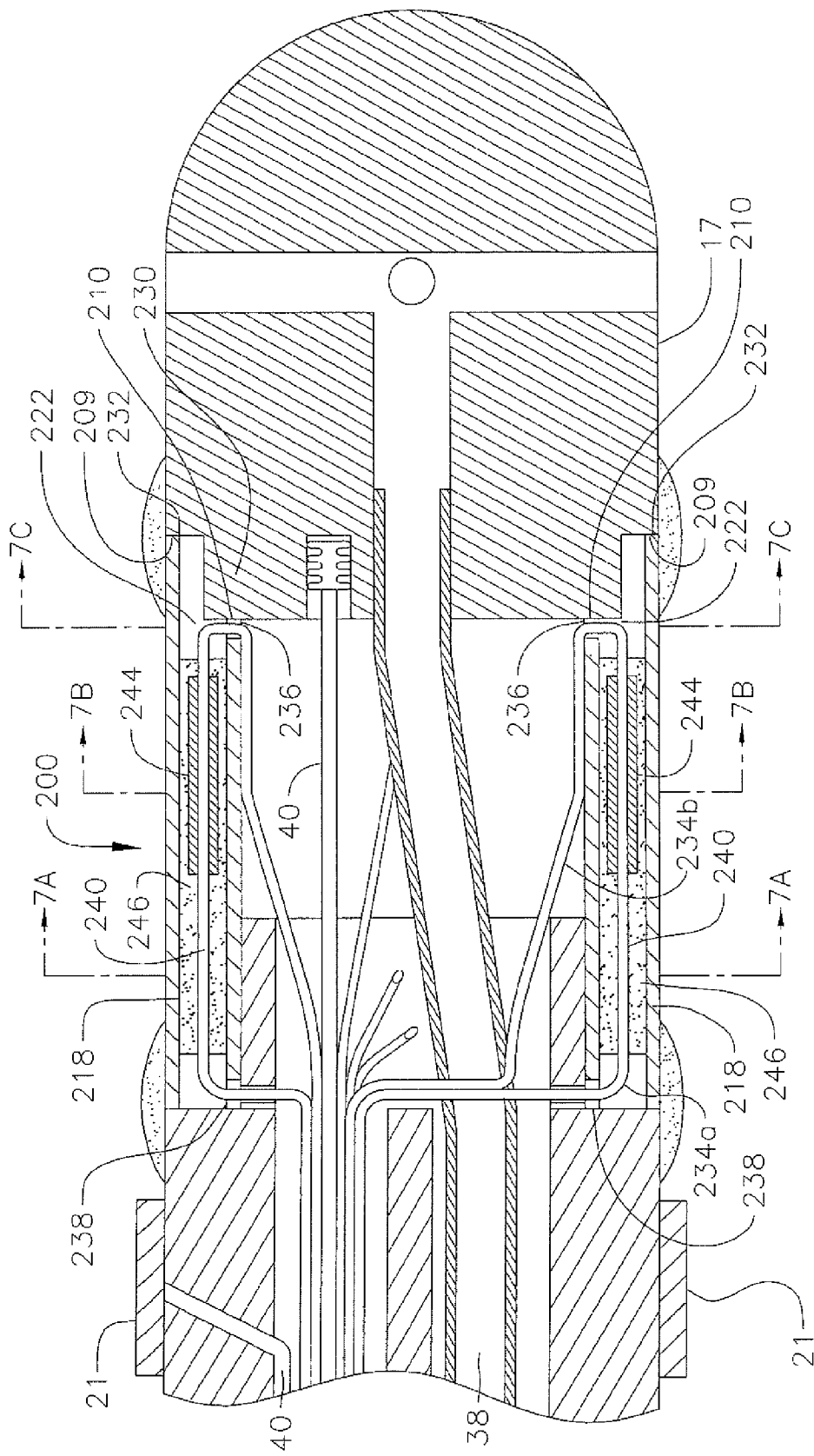
FIG. 7 is a side cross-sectional view of an alternate embodiment of a distal tip section, including a tip electrode and a contact force sensor susceptible to strain and stress.
Figure 7A:
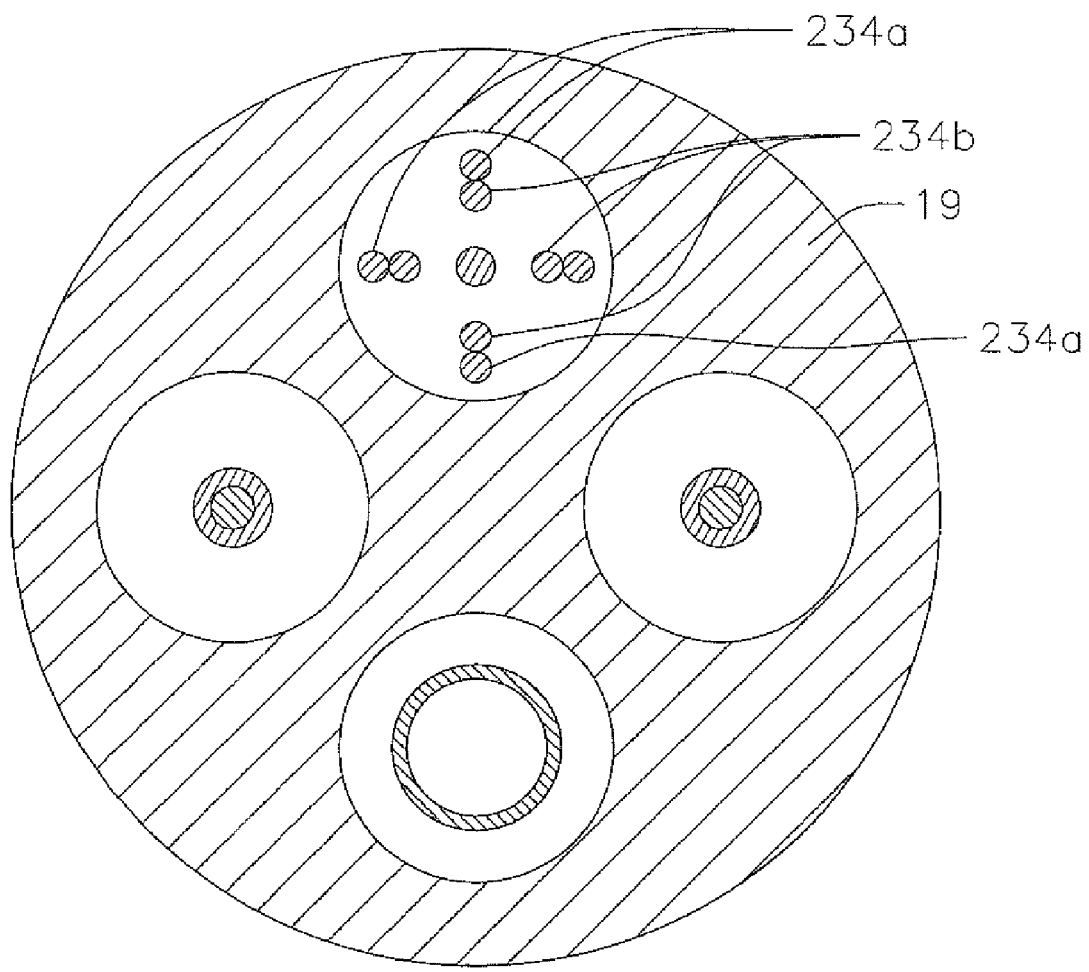
FIG. 7A is an end cross-sectional view of an embodiment of a deflectable intermediate section adapted for use with the embodiment of the distal tip section of FIG. 7.
Figure 8:
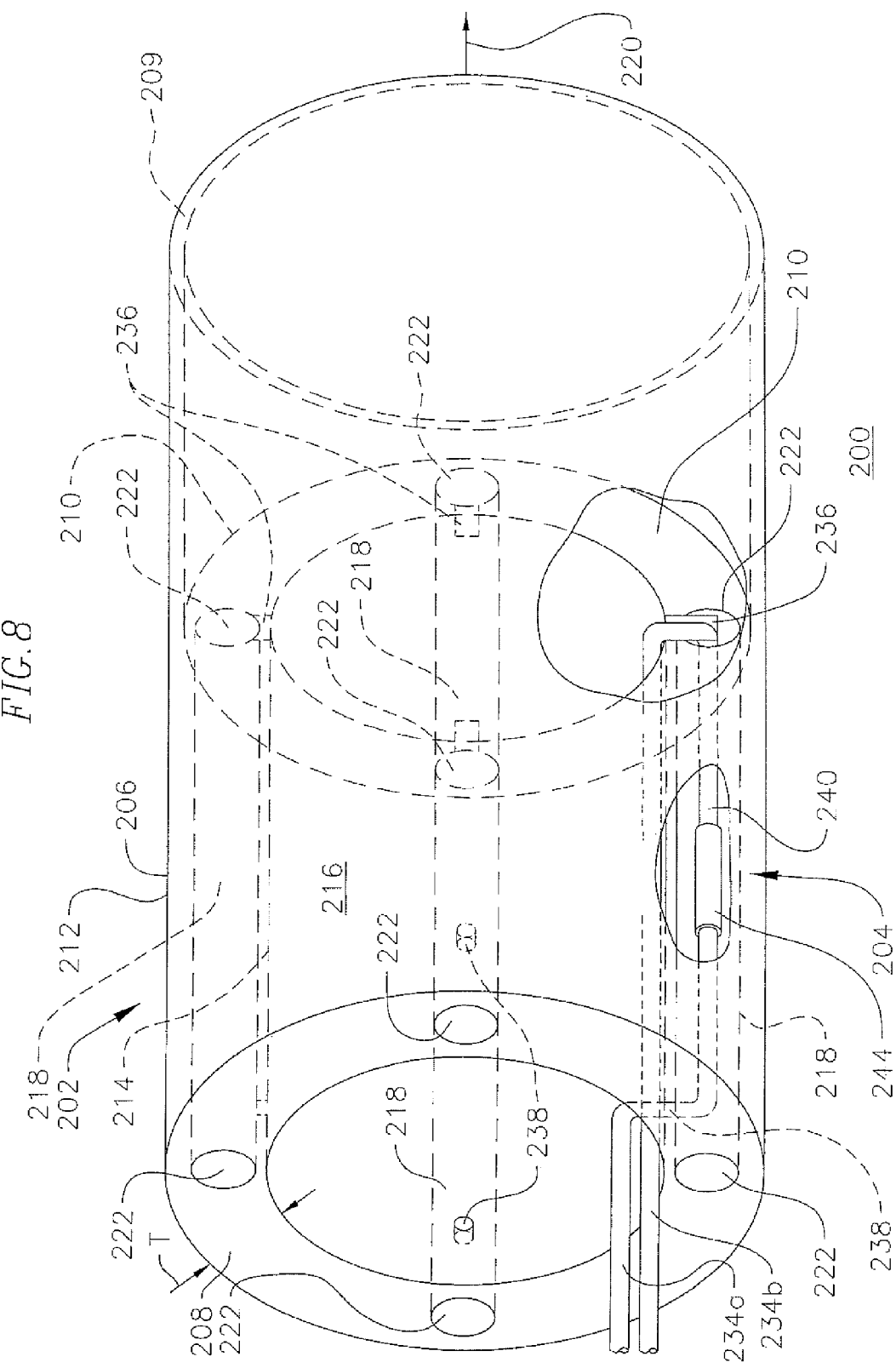
FIG. 8 is a perspective view of the embodiment of the contact force sensor of FIG. 7.

With reference to FIG. 7, the outer distal end 209 of the force sensor receives a proximal stem 230 of the tip electrode. The tip electrode and the force sensor are sized so that the outer distal end 209 of the force sensor 200 abuts a proximal circumferential end 232 of the tip electrode and a proximal end of the stem 230 abuts the inner distal end 210 of the force sensor, so that a force vector applied to the tip electrode 17 is transmitted to the force sensor 200 at the outer distal end and inner distal end of the force sensor.

Extending through each passage 218 is a small diameter strain sensing tensile member 234 ("tensile member" and "wire" used interchangeably herein), e.g., a small diameter electrically conductive wire such as a polycrystalline copper wire. In the illustrated embodiment, each strain sensor wire has a U-shaped bend at the inner distal end of the force sensor body that, for ease of discussion purposes) defines a first wire portion 234a and a second wire portion 234b. An inwardly facing notch or recess 236 is provided in each opening 222 at the inner distal end 210 of the body so that the wires are not pinched between the stem 230 and the inner distal end 210 of the force sensor. Likewise, a through-hole 238 is provided near the proximal end of each passage so that the wires are not pinched between force sensor 200 and the circumferentially-notched distal end of the tubing 19 of the deflectable intermediate section 14.

In one embodiment, the housing 202 has an outer diameter of about 0.095 inches. The wall 206 of the body has a thickness of about 0.025-0.028 inches. The axial passage 218 has a diameter of about 0.010-0.014 inches. Each strain sensing tensile member 234 has a diameter of about 0.004-0.006 inches, with a "working" strained length of about 0.10-0.20 inches.

A segment 240 of each first wire portion 234a extends through the passage 218 and a subsegment thereof is provided with a magnetic coating, film or layer 244. The segments inclusive of the magnetic films 244 are embedded in the passages by a bonding adhesive or cement 246. As understood by one of ordinary skill in the art, the composition of the magnetic film 244 is controlled so its properties are strain sensitive. The high permeability film, which is deposited onto a wire, dominates the inductance of the wire, so measuring either the inductance or the loss in the wire monitors its magnetic properties. The ability to plate the magnetic film uniformly on the small diameter wire allows the magnetic film to be easily driven to saturation. Thus, losses in the film are monitored. Since the magnetic properties of the film are strain sensitive, the wire senses changes in strain. Because the strain sensing wires are inert, they are embedded in the passages. As also understood by one of ordinary skill in the art, each strain sensing wire utilizes the magnetic field produced by a current in the wire. This field sees a shape of a circumferentially continuous magnetic coating. However, external fields see another shape of an axially or diametrically discontinuous coating. The self-demagnetizing effects of these shapes significantly reduce the effects of these external fields. The effects due to normally encountered external magnetic fields can therefore be virtually eliminated by patterning the film into small axially separated segments without affecting the field produced by the current. The length of the magnetic film deposited around the wire determines the active strain region of the sensor. In one embodiment, the length is about 0.18-0.20 inches long. Suitable strain sensors are available from Sensortex, Inc. of Kennett Square, Pa.

Each segment 240 extending through a passage 218 is pre-strained ("pre-strained" and "pre-stressed" used interchangeably herein) with an applied tensile force (e.g., 1000 micro strains) during the application and drying/curing of the bonding adhesive embedding the segment in the passage. The pre-straining of the wires serves to remove signal dead band area and to increase portion (or sensor signal span length). A controlled uniform tension is applied to each sensor wire for sensing symmetry in the force sensor. The plurality of wires in the force sensor can range between about two and ten. In the illustrated embodiment, there are four wires that are positioned at about 90 degrees about the longitudinal axis 220 of the force sensor.

In the illustrated embodiment, the first portion 234a of each strain sensor wire extends through the central lumen 18 of the catheter body, the first lumen 30 of the deflectable intermediate section 14 and a respective passage 218 of the force sensor 200. The second portion 234b of each strain sensor extends through the interior space 216 of the force sensor 200, the first lumen 30 of the deflectable intermediate section 14 and the central lumen 18 of the catheter body 12. Deformation of the body of the force sensor results in a change in the strain amplitude to the strain sensors 204. Each strain sensor of the force sensor 200 is connected to a power supply and appropriate circuit(s) and/or processor(s) that provide AC currents through the wires and receives their voltage outputs to detect inductance or loss for determining a 3-D applied force vector applied to the tip electrode.

It is understood by one of ordinary skill in the art that when force vectors act upon the tip electrode, they are transferred to the cylindrical body of the force sensor which slightly deforms and thus imparts a change in strain to the strain sensors. The small size and symmetrical profile of each strain sensor allow the magnetic film to be easily driven into saturation with modest current levels. The resulting hysteresis loss dominates the impedance of the strain sensors and is highly stress dependent. Measuring either the inductance or the hysteresis loss in the wires monitors their magnetic properties. This loss is a nonlinear response curve with respect to current and produces high frequency voltage spikes that can be detected with analog or digital signal extraction circuits (see FIG. 9).

The body can be constructed of any material that is biocompatible, temperature stable and sufficiently rigid to experience deformation with stress and strain, including PEEK polyetheretherketone, self-reinforced polyphenylene, polyphenylsulfone or liquid crystal polymer. The bonding adhesive that bonds the strain sensors in the passages should have an elastic modulus and coefficient of thermal expansion that is comparable to the body construction material.

As illustrated in FIGS. 7 and 8, distal and proximal ends of each strain sensor wire is accessible for current input and voltage output to and from a controller adapted to send, receive and process electrical input and output signals to and from the distal section 15 for mapping, ablation and/or force sensing by means of a microprocessor applying program algorithms with force sensing solutions.

Figure 10:
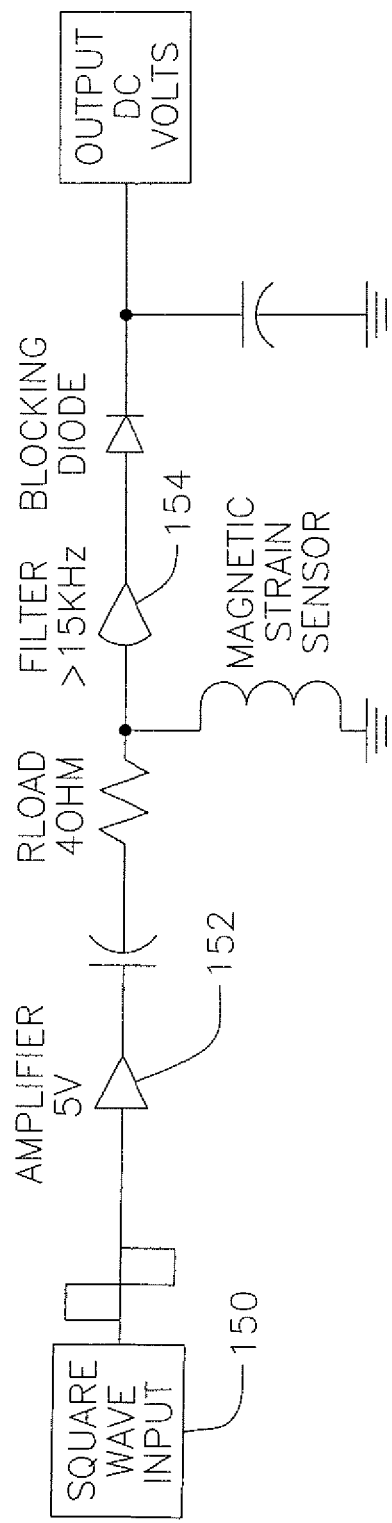
FIG. 10 is schematic of an embodiment of a sensor drive circuit with square wave input filter (high pass) and rectifier/DC voltage averager.

FIG. 10 illustrates an embodiment of a drive circuit for the force sensor 200, where the force sensor is driven with a square wave oscillator 150 (frequency input range about 5-50 KHz) amplified with an operational amplifier 152 (drive voltage about 1-5 volts and RMS current of about 200-800 mA). The circuit also includes a second operational amplifier 154 that acts as a high pass filter (filters signals greater than 15 KHz) that eliminates the large voltage component at the drive frequency consisting of the sensor wire resistance and the inductive component of the magnetic coating. The inductance changes slightly when the sensor is strained, but the change in loss factor is much larger. The DC output voltage decreases with increasing sensor strain.

Figure 11:
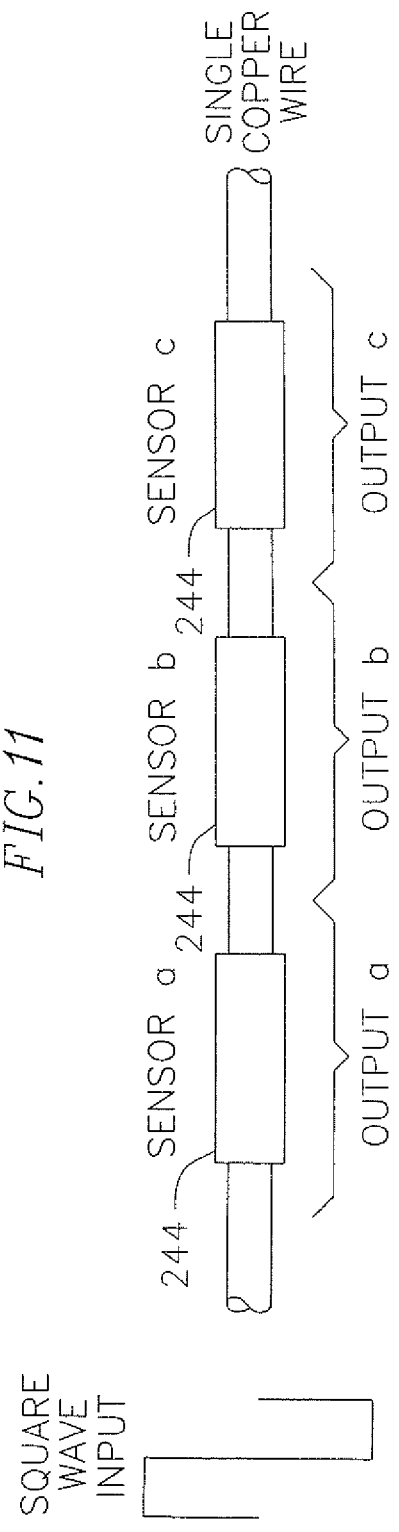
FIG. 11 is a perspective view of an alternate embodiment of a contact force sensor with multiple magnetic coatings.

The present invention includes an alternate embodiment in which multiple sensors (magnetic films) are provided on each wire. However, it is understood that the voltage across each sensor is measured and thus a wire connection point at each sensor end is provided. A single wire multiple sensor configuration results in fewer wires since there is only a single current input, but multiple wire bond connections to a wire, including a number 38 wire, may not be as reliable or cost effective as utilizing a multitude of two-wire sensors for strain measurement. FIG. 11 illustrates an embodiment of a single wire multiple sensor configuration, for example, a single copper wire with three magnetic films 244 resulting in three force sensors 200a, 200b, 200c, each providing a respective output Output a, Output b, Output c.

The voltages, currents and frequencies required for sensor operation range from about 1-5 volts, 200-800 mA (square wave form) at frequencies ranging from about 5 KHz 50 KHz. As the sensor strain increase, the resulting spike at the beginning and end of each square wave is reduced (see FIG. 9). A strain sensor voltage output filtering circuit combined with a high speed operational amplifier based open or closed loop peak pulse detector circuit may be used to convert the sensor strain peak voltage values into a stable DC voltage output (see FIG. 10).

Figure 9:
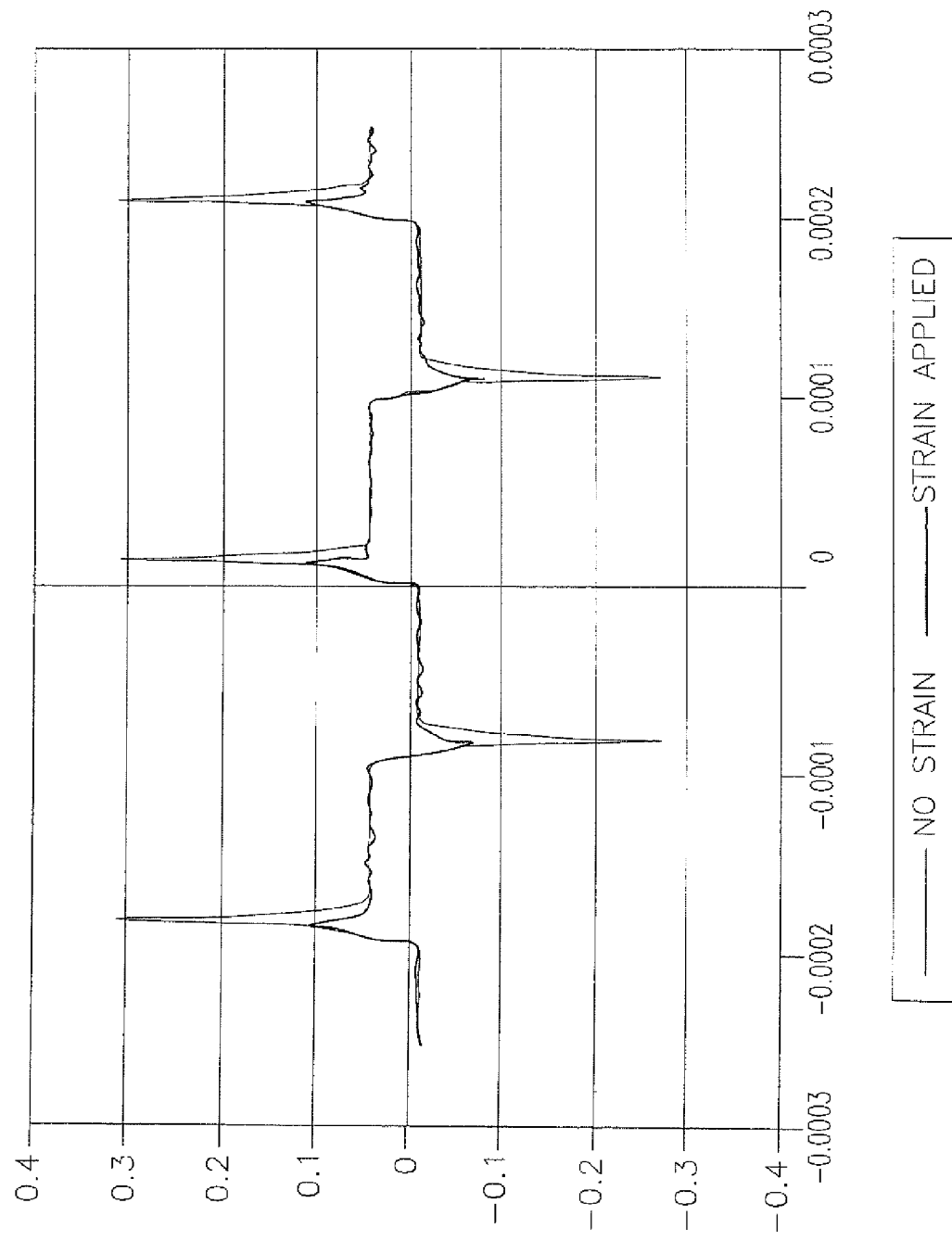
FIG. 9 is a graph comparing voltage output of strain sensors of a contact force sensor of FIG. 7 as a function of time, for square wave excitation, with and without load.

It is understood that the embodiment of the catheter of FIGS. 7-9 can also include a connection tubing 53 between the intermediate section 14 and the force sensor 200, in which an electromagnetic position sensor 48 is housed proximal of the force sensor 200. A cable 46 for the sensor 48 can pass through the first lumen 30 of the intermediate section 14 before it reaches the control handle 16.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter, comprising:
    an elongated catheter body;
    a deflectable section distal the catheter body;
    a tip electrode distal the deflectable section; and
    a contact force sensor between the deflectable section and the tip electrode, the force sensor comprising a cup shaped body having a generally cylindrical wall, a plurality of radial spokes, a beam member, and at least one strain gage mounted on one of the radial spokes, the radial spokes converging at a location on the body from which the beam member extends,
    wherein an end of the beam member is connected to the tip electrode.

2. A catheter of claim 1, wherein a gap exists between the tip electrode and the body of the force sensor.

3. A catheter of claim 1, wherein each radial spoke has at least one strain gage mounted thereon.

4. A catheter of claim 1, wherein each radial spoke has at least two surfaces and each surface has at least one strain gage mounted thereon.

5. A catheter of claim 1, comprising at least three radial spokes.

6. A catheter of claim 1, further comprising an irrigation tubing that extends through the beam member.

7. A catheter of claim 1, further comprising apertures between the radial spokes.

* * * * *